(12) United States Patent
Shroff et al.

(10) Patent No.: US 9,554,577 B2
(45) Date of Patent: *Jan. 31, 2017

(54) HERBICIDAL FORMULATION

(75) Inventors: Jaidev Rajnikant Shroff, Maharashtra (IN); Vikram Rajnikant Shroff, Maharashtra (IN); Prakash Mahadev Jadhav, Maharashtra (IN); Christian Becker, King of Prussia, PA (US)

(73) Assignee: UPL LIMITED, Mumbai, Maharashtra (IN)

(*) Notice: Subject to any disclaimer, the term of this patent is extended or adjusted under 35 U.S.C. 154(b) by 54 days.

This patent is subject to a terminal disclaimer.

(21) Appl. No.: 14/238,009

(22) PCT Filed: Sep. 29, 2011

(86) PCT No.: PCT/IB2011/002280
§ 371 (c)(1),
(2), (4) Date: Feb. 10, 2014

(87) PCT Pub. No.: WO2013/021229
PCT Pub. Date: Feb. 14, 2013

(65) Prior Publication Data
US 2014/0200141 A1    Jul. 17, 2014

(30) Foreign Application Priority Data
Aug. 10, 2011 (IN) .......................... 2251/MUM/2011

(51) Int. Cl.
- *A01N 25/28* (2006.01)
- *A01N 25/04* (2006.01)
- *A01N 33/18* (2006.01)
- *A01N 43/80* (2006.01)

(52) U.S. Cl.
CPC .............. *A01N 43/80* (2013.01); *A01N 25/04* (2013.01); *A01N 25/28* (2013.01); *A01N 33/18* (2013.01)

(58) Field of Classification Search
None
See application file for complete search history.

(56) References Cited

U.S. PATENT DOCUMENTS

| 4,871,392 A | 10/1989 | Morgan et al. |
| 5,461,027 A | 10/1995 | Bergman |
| 5,583,090 A | 12/1996 | Stern et al. |
| 5,597,780 A | 1/1997 | Lee et al. |
| 5,705,174 A | 1/1998 | Benoff et al. |
| 6,440,902 B1 * | 8/2002 | Szamosi ............... A01N 25/28 504/138 |
| 2001/0041659 A1 * | 11/2001 | Becker ................. A01N 43/80 504/140 |
| 2010/0323892 A1 * | 12/2010 | Levy ....................... B01J 13/14 504/118 |

FOREIGN PATENT DOCUMENTS

| CN | 101057582 | 10/2007 |
| WO | WO 2011/095859 | 8/2011 |

OTHER PUBLICATIONS

International Search Report and Written Opinion from International Application No. PCT/IB2011/002280 mailed Jan. 5, 2012.
Martin et al., "Sodium and chloride ions contribute synergistically to salt toxicity in wheat", *Biologia Plantarum*, vol. 37, No. 2, 1995, pp. 265-271.
Xu et al., "Effect of 18% Pendimethalin + Clomazone WP against Weeds in Transplanted Rice", *Modern Agrochemicals*, vol. 6, No. 3, 2007, pp. 44-47. (English Translation).

* cited by examiner

*Primary Examiner* — Tracy Vivlemore
*Assistant Examiner* — Monica Shin
(74) *Attorney, Agent, or Firm* — Merchant & Gould P.C.

(57) ABSTRACT

A capsule suspension formulation comprising microencapsulated pendimethalin comprising a herbicidally effective amount of pendimethalin being encapsulated within a polymeric wall, said polymeric wall being in-situ formed by an interfacial polymerization reaction occurring between a first phase dispersed in a second phase, at least one of said first and second phases being characterized in comprising a pre-defined amount of at least one alkali or alkaline earth metal salt of an organic acid; and a herbicidally effective amount of a second herbicide.

4 Claims, 5 Drawing Sheets

US 9,554,577 B2

HERBICIDAL FORMULATION

This application is a National Stage Application of PCT/IB2011/002280, filed 29 Sep. 2011, which claims benefit of Serial No. 2251/MUM/2011, filed 10 Aug. 2011 in India and which applications are incorporated herein by reference. To the extent appropriate, a claim of priority is made to each of the above disclosed applications.

FIELD OF INVENTION

The present invention relates to a capsule suspension formulation comprising pendimethalin in combination with clomazone. More particularly, the present invention relates to a storage stable, improved non-staining and non-volatile capsule suspension formulation comprising pendimethalin in combination with clomazone.

BACKGROUND AND PRIOR ART

Pendimethalin is a dinitroaniline herbicide having chemical formula [n-(1-ethylpropyl)-3,4-dimethyl-2,6-dinitrobenzenamine). It was first registered for use in the United States in 1974. It is a selective herbicide which controls certain broadleaf weeds and grassy weed species in crop and non-crop areas. It is applied to soil preplant, preemergence, and postemergence with ground and aerial equipment.

Pendimethalin is an orange yellow crystalline solid with a melting point of 54-58° C. It is soluble in chlorinated hydrocarbons and aromatic solvents such as methylene chloride, acetone and xylene. Pendimethalin is stable under acidic and alkaline conditions.

Pendimethalin is currently available in various different agrochemical formulation types such as emulsifiable concentrate (21.9% to 42.3%), liquid (34.4%), granular (0.7% to 2.0%), soluble concentrate/liquid (22.0%), water dispersible granules, dry flowable (up to 60.0%), capsule suspension and wettable powder (50.0%). Thus, there are many formulation choices available to a formulator setting out to prepare a desired formulation of pendimethalin.

The different formulations applicable to an agrochemical differ in their effectiveness on the desired weeds, effects the tolerance of the turf and ornamentals to the herbicide, differ in their cost advantages, differ in the drift potential of the herbicide and also differ in the ease of application and compatibility with the application equipment. Another challenge to the skilled formulator is the selection of an appropriate surfactant. Surfactants are known to increase the rate of absorption of the herbicide in the weedy species but also increase the potential for plant injury to the desirable plants during herbicide drift. Yet another challenge before a skilled formulator setting out to obtain a formulation containing pendimethalin is selecting either a granular or a sprayable formulation.

Pendimethalin has been conventionally available in both granular and sprayable forms, which may differ in the degree of weed control. However, it is often advantageous to obtain a sprayable formulation containing certain herbicides due to inherent advantages of a sprayable formulation.

The granular formulations exhibit relatively low foliar absorption because most of the applied granules fall through the leaf canopy to the soil below. In contrast, sprayable products achieve good coverage and adhere better to the foliage, providing relatively good weed control. It has also been observed that a granular product comprises a greater relative amount of the inert ingredients comparative to a sprayable formulation. Thus, the amount of the formulated product to deliver the same dosage of the active ingredient is much greater with granules resulting in higher shipping and packaging costs.

An advantage of the sprayable formulation over granules is more uniform application achieved with the sprayable formulations. The granular formulations are usually difficult to apply uniformly, especially those that contain a relatively high concentration of active ingredient. Thus, it is more often advantageous to formulate sprayable formulations of certain agrochemicals.

However, phytotoxicity of some of the sprayable formulations including pendimethalin has been reported. It is desirable to provide formulations containing pendimethalin that do not display or reduces the extent of phytotoxicity.

Another challenge that relates to dinitroaniline herbicides, and pendimethalin in particular, is the potential for staining the sidewalks and other locations where the herbicide is applied. The active ingredient herbicides of the dinitroaniline class have a yellowish or yellowish-orange color. It is further known that granular formulations often do not stain badly, whereas a liquid formulation may cause more serious staining. Moreover, granules are easy to sweep or blow from concrete surfaces, whereas overspray need to be washed off before it dries.

Thus, it is desirable to provide sprayable formulations containing pendimethalin that substantially reduce the incidence of staining.

U.S. Pat. No. 4,871,392, discusses under the background thereof, that pendimethalin is known to exist in polymorphic forms as orange and yellow crystals. This patent further discusses that pendimethalin is a pesticide that is difficult to formulate owing partly due to the unique staining problems associated with it. This patent further discusses that the presence of pendimethalin in the orange macrocrystal form results in large elongated crystals in final formulations. Moreover, when pendimethalin in the orange macrocrystal form is found in compositions, very large, elongated crystals (about 3000 microns in length) appear in final product, resulting in instability, difficulty in processing and unreliability of usage apart from the severe staining further compounded by a severe clogging of nozzles.

U.S. Pat. No. 5,705,174 discloses microencapsulated pendimethalin formulations i.e. an aqueous concentrate composition of pendimethalin particles which are encapsulated by a polymeric wall material, which show a reduced tendency to form large crystals. These compositions also have improved storage stability. Unfortunately, it has been seen that microencapsulation of pendimethalin tends to slow the release of the active ingredient. U.S. '174 teaches an aqueous capsule suspension formulation of pendimethalin, which contains about 456 grams of active ingredient per liter. The encapsulation of pendimethalin allows for the elimination of organic solvents in the product. The elimination of organic solvents reduces odor, staining to a certain extent, volatility and surface residue adhesion as compared to existing emulsifiable concentrate formulations of pendimethalin. Moreover, the microencapsulated pendimethalin formulation is stable under conditions of freezing and thawing and is compatible with liquid and dry fertilizer. However, the existing problem of staining, phytotoxicity and corrosiveness is not adequately addressed by the disclosure of U.S. Pat. No. 5,705,174.

Moreover, this patent essentially teaches a microencapsulated formulation of pendimethalin containing an inorganic salt, which is added prior to microcapsule formation. It is disclosed that the addition of an inorganic salt or mixtures thereof prior to the microcapsule formation provides a visibly cleaner microcapsule as more of the colored active ingredient is encapsulated, which is therefore unable to stain the external surfaces of the microcapsules.

These microcapsules are also stated to be less prone to breakage than the microcapsules prepared by the conventional methods. Examples of inorganic salts taught by this patent are sodium chloride, calcium chloride, potassium chloride, sodium nitrate, magnesium sulfate and/or sodium sulfate.

However, these inorganic salts are not without additional disadvantages. The use of an inorganic salt such as sodium chloride even to the extent of 0.1-0.5% has been shown to aggravate the already existing phytotoxicity of pendimethalin which is evident from "Sodium and chloride ions contribute synergistically to salt toxicity in wheat," Biologia Plantarium, 37 (2); 265-271, 1995. Here, Martin et al., studied the effects of supplying excess mineral salts, involving sodium as a cation and a range of counter-anions, including chloride on the growth and photosynthetic capacity of a salt susceptible bread wheat. It was found that the synergistic effect of sodium and other alkali and alkaline earth metals with chlorine shows that neither of these ions is alone responsible for the salt stress induced damage in plants.

Moreover, these inorganic salts dissociate and/or dissolve in water and increase the hardness of water. The increased water hardness further reduces the temperature and suspension stability of microencapsulated pendimethalin. Moreover, the polymeric capsule wall of the disclosed microencapsulated pendimethalin is still susceptible to breakage to an appreciable extent. Thus, the problem of staining continues to plague the existing state of the art.

A need remains in the art for microencapsulated formulations of pendimethalin having improved non-staining property with reduced phytotoxicity problems.

Clomazone is the common name for the herbicide 2-(2-chlorophenyl) methyl-4,4-dimethyl-3-isoxazolinone. It is a colorless to light brown and viscous liquid above room temperature, which forms a white crystalline solid when cooled. It is not flammable in nature.

Clomazone has the following chemical structure:

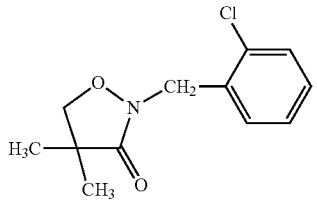

Clomazone is a highly effective herbicide, but unfortunately is also highly volatile. The amount of clomazone applied to the soil in a target area may move to adjacent areas and cause discoloration. This discoloration is typically in the form of whitening or some degree of bleaching, of a variety of crops, trees, or decorative plants. This bleaching, which is also indicative of the mode of action of the herbicide, may be temporary when plants are exposed to sufficiently low concentrations. However, bleaching of the crops, trees or decorative plants is undesirable even when it does not result in the destruction of the plant.

Clomazone is a broad spectrum herbicide used for control of annual grasses and broadleaf weeds in cotton, peas, pumpkins, vegetables, sweet potatoes, tobacco, winter squash and fallow wheat fields. It can be applied early preplant, preemergent or preplant-incorporated depending on the crop, geographical area and timing. Because clomazone is an inhibitor of plant pigments, users must exercise caution to avoid drift or vapors which may cause bleaching damage to non-target foliage.

Clomazone is relatively stable to degradation by UV light. It is highly volatile and can drift during or after application, causing damage to sensitive, non-target plants such as ornamental trees and shrubs, roses, small grains, alfalfa, sunflowers, and vegetable crops. Clomazone is slightly soluble in water, but it has a moderate tendency to adsorb to soil particles. It therefore has a low to moderate potential to contaminate groundwater.

Hitherto, a non-encapsulated emulsifiable concentrated formulation of clomazone has been available. However, upon application of the conventional emulsifiable concentrated formulation, the sensitive plants surrounding the intended targets of application displayed varying degrees of whitening due to the high volatility of clomazone. Thus, an encapsulated formulation of clomazone was desirable which was believed to be capable of reducing the volatility of clomazone and improve the active component delivery to the targeted plants.

Attempts to prepare formulations of encapsulated clomazone by encapsulating clomazone in polyurea and polyamide polymeric shells frequently resulted in formulations that not only gave little or no reduction in volatility, but had poor physical characteristics such as undesirable agglomeration of the capsules or separation of phases or breaking of the capsule wall on spray application which results into failure to achieve the volatility reduction. It was thus desirable to provide a herbicidal formulation having an improved plasticity of the polymeric shell wall to reach an acceptable release rate of the active ingredient clomazone. It is believed that an improvement in plasticity of the polymeric shell wall would substantially reduce the permeation of the shell wall to the active ingredient and possibly limit the breakage of the capsule wall on spray application, which would consequently achieve a substantial reduction in volatility of the formulation.

Another challenge during the encapsulation of clomazone had been its relatively higher water solubility. The known encapsulation methods involve a reaction between an aqueous phase and an organic phase. It was found that the low/mild solubility of clomazone in water did result into poorly defined droplets and also increased the amount of the free active ingredient in the aqueous phase. An increased amount of clomazone in the aqueous phase could contribute to an increased initial "burst effect" administration of clomazone thereby aggravating the risk of plant phytotoxicity and off-target injury due to the volatility of the free clomazone.

U.S. Pat. No. 5,583,090 is directed to a sprayable herbicidal formulation comprising an aqueous liquid having suspended therein a multitude of solid microcapsules having a capsule wall of a porous polymer encapsulating clomazone dissolved in a high boiling inert organic solvent.

U.S. Pat. No. 5,597,780 teaches a process for preparing herbicidally effective formulations of clomazone by microencapsulating clomazone by interfacial polymerization reaction between an aqueous phase and an organic phase. The organic phase essentially comprises a hydrocarbon solvent.

These patents disclose that when the formulations taught therein are sprayed onto one plot containing vegetation, vapor transfer of the herbicide to a nearby plot containing vegetation is effectively suppressed without substantial sacrifice of herbicidal efficacy of the herbicide in the plot to which the spray is applied. However, the problem of reducing the permeability of the polymeric shell wall to the active ingredient consequently limiting the rupture of the capsule wall on spray application and substantially reducing the volatility of the microencapsulated formulation of clomazone still remains a problem. Further, this problem continues to remain irrespective of the chemical nature of the polymeric shell wall such as a polyamide, polyurea, polyurethane, polycarbonate, melamine resin, melamine urea resin, gelatine/gum arabic or cross linked or non-crosslinked combinations thereof. Moreover, the use of an organic solvent is not always desirable.

The regulatory bodies throughout the world are slowly imposing stringent restrictions on the quantity and choice of solvents in a formulation. Typical organic solvents used in pesticide formulations usually have a low boiling point and evaporate easily or can be removed by distillation, leaving the dissolved substance behind. Solvents are usually clear and colorless liquids and many have a characteristic odor.

The low vapor pressure of traditional solvents generally makes them hazardous because these solvents evaporate easily into the air exposing the factory workers to inhalation hazards. Additionally, some solvents add to damage of the earth's atmosphere as they eventually oxidize and create carbon dioxide, a green house gas with potential impact on global warming.

Most organic solvents have a lower density than water, which means they are lighter and will form a separate layer on top of water. Further, most organic solvents are flammable or highly flammable, depending on their volatility. Mixtures of solvent vapors and air can explode. Solvent vapors are heavier than air, they will sink to the bottom and can travel large distances nearly undiluted. Many solvents can lead to a sudden loss of consciousness if inhaled in large amounts.

A major pathway leading to adverse health effects arises from spills or leaks of solvents that reach the underlying soil. Since solvents readily migrate substantial distances, the creation of widespread soil contamination is not uncommon. This is particularly a health risk if aquifers are contaminated. Some solvents including chloroform and benzene are carcinogenic. Many others can damage internal organs like the liver, the kidneys, or the brain.

In agrochemical formulations, the organic solvents are usually present in the smaller and/or greater amount depending upon the type of formulation and agrochemicals. The use of routine organic solvents poses problems while using, manufacturing, storing, transporting the solvents and the products comprising them.

In general, agrochemical formulations especially liquid form comprises either inorganic or organic solvents. Most of the known organic solvents known in the art are non-biodegradable and highly flammable. Organic solvents-based agrochemical formulations generally use a solvent that is preferably water-immiscible to dissolve the active component completely and produces a clear homogenous liquid free from extraneous matter. Alternatively, organic solvents typically have a low flash point, are non-biodegradable, cause skin irritation and possess medium or high evaporation rate etc., but provide a clear homogenous liquid. The known agrochemical compositions further include at least a surfactant wherein the performance and dosage of the included surfactant is based on the active content and solvent in the formulation, type of active ingredient, and solubility of the active ingredient in the solvent and the required emulsion performance of the final product. In many cases, the emulsion performance shown by organic solvent can be superior to that of inorganic solvents. However, certain challenges exist with solvent usage because the solvent used are non-biodegradable and also require a large quantity of the surfactant to emulsify the formulation during dilution, prior to the application on crops. With organic solvents, during manufacturing, packing, storage, transport and use the risk of skin irritation, non biodegradability, fire hazard, air and soil pollution exists.

Moreover, the regulatory bodies around the world are now considering the public disclosure of all pesticide inert ingredients including the solvents. These regulatory bodies are making it mandatory to identify all the inert ingredients including solvents etc. on the product label. Thus, a formulation which substantially reduces or completely eliminates the need of an organic solvent to be present within the formulation and is thus completely biodegradable would be a highly desirable formulation from a regulatory and customer acceptance point of view.

Accordingly, there is a need in the art for an agrochemical formulation that is devoid of an organic solvent or that includes an organic solvent in minimum required quantities. The present invention described herein provides such an agrochemical formulation.

It is generally desirable to prepare formulations of agrochemicals having minimum volatility to reduce the incidence of off-site injury in order to avoid any unintended pesticidal activity. The volatility of agrochemical formulations is known to cause various off-site unintended injuries. Thus, it is another challenge in the art to prepare storage stable formulations of agrochemicals having a substantially reduced volatility without compromising the other desirable properties of the formulation.

The use of herbicide combinations is a widespread and documented practice in the agricultural community. Herbicidal combinations offer significant advantages over individual applications including improved and extended weed control, reduced herbicide rates and application costs, shorter contact times for improved results in flowing water, less stringent use restrictions, improved selectivity, improved spectrum of weeds controlled, reduced cost and reduced residue problems. However, identifying appropriate herbicide application rates and combinations is essential to achieve synergistic weed control. The different individual problems discussed above for pendimethalin and clomazone make it further difficult for a skilled formulator to co-formulate the two herbicides in a manner that simultaneously reduces the staining in pendimethalin and volatility in clomazone.

The article Effect of 18% pendimethalin+clomazone WP against weeds in transplanted Rice, XU Xiu-jie, Zhang Xiang-quan (Jilin Yiheng Pesticide Co. Ltd., Jilin Gongzhuling 136100, China; Jilin Ruiye Pesticide Co. Ltd., Jilin Gongzhuling 136100, China) evaluated the control of 18% pendimethalin+clomazone WP against weeds in transplanted rice. It was found that excellent weed control was achieved when 18% pendimethalin+Clomazone WP was applied at 5 to 7 days after transplanting and with the dosage of 0.175-0.351 kg/hm². This reference does not address the staining problem associated with pendimethalin and volatility and associated off-site injury with clomazone, particularly when the two herbicides are encapsulated together.

There is thus a need in the art for an encapsulated formulation of pendimethalin and clomazone that overcomes the aforesaid problems in the art.

ADVANTAGES OF THE INVENTION

Thus, an advantage of the present invention is a capsule suspension formulation of pendimethalin in combination with clomazone.

Another advantage of the present invention is a storage stable, improved non-staining and non-volatile capsule suspension formulation comprising pendimethalin in combination with clomazone.

Another advantage of the present invention is a non-staining, non-phytotoxic capsule suspension formulation comprising pendimethalin in combination with clomazone, wherein the volatility of clomazone is substantially reduced.

Another advantage of the present invention is a non-corrosive capsule suspension formulation comprising encapsulated pendimethalin and clomazone.

There is thus a need in the art for an encapsulated formulation of pendimethalin and clomazone that overcomes the aforesaid problems in the art. The remaining portion of the description offers at least one of these and/or any other advantages.

SUMMARY OF THE INVENTION

Thus, in one aspect, the present invention provides a capsule suspension formulation comprising;
  microencapsulated pendimethalin comprising a herbicidally effective amount of pendimethalin encapsulated within a polymeric wall, said polymeric wall being in-situ formed by an interfacial polymerization reaction occurring between a first phase dispersed in a second phase, at least one of said first and second phases being characterized in comprising a pre-defined amount of at least one alkali or alkaline earth metal salt of an organic acid; and
  a second herbicide.

In another aspect, the present invention provides a capsule suspension formulation of microencapsulated pendimethalin and a second herbicide being clomazone;
  said microencapsulated pendimethalin comprising a herbicidally effective amount of pendimethalin being encapsulated within a polymeric wall, said polymeric wall being in-situ formed by an interfacial polymerization reaction occurring between a first phase dispersed in a second phase, at least one of said first and second phases being characterized in comprising a pre-defined amount of at least one alkali or alkaline earth metal salt of an organic acid; and
  said second herbicide clomazone being either co-microencapsulated with pendimethalin or being unencapsulated or being microencapsulated separately and mixed with microencapsulated pendimethalin in a predetermined ratio.

In another aspect, the present invention provides a process for the preparation of a capsule suspension formulation, said process comprising:
  (a) forming an aqueous solution comprising at least one surfactant and a pre-defined amount of at least one alkali or alkaline earth metal salt of an organic acid;
  (b) forming an organic phase by melting a herbicidally effective amount of pendimethalin active ingredient and a second herbicide and adding a predetermined amount of polyisocyanate wall forming component;
  (c) dispersing said organic phase in said aqueous solution to obtain an emulsion to form an interface between the discrete droplets of organic phase and the aqueous phase; and
  (d) maintaining said emulsion for a sufficient period of time to allow substantial completion of the self-polymerization reaction of polyisocyanate such that said liquid droplets in the organic phase are converted to capsules comprising polyurea shells enclosing pendimethalin active ingredient and said second herbicide.

In another aspect, the present invention provides a process for the preparation of a capsule suspension formulation, said process comprising:
  (a) forming an aqueous solution comprising at least one surfactant and a pre-defined amount of at least one alkali or alkaline earth metal salt of an organic acid;
  (b) forming an organic phase by melting a herbicidally effective amount of pendimethalin active ingredient, at least a second herbicide and adding a predetermined amount of a first wall component to said organic phase;
  (c) dispersing said organic phase in said aqueous solution to obtain an emulsion; and
  (d) adding a second wall forming component to said emulsion such that said second wall forming component reacts with said first wall forming component comprised within said emulsion to polymeric wall encapsulating at least said herbicidally effective amount of pendimethalin active ingredient and said second herbicide.

DESCRIPTION OF INVENTION

Figure 1:
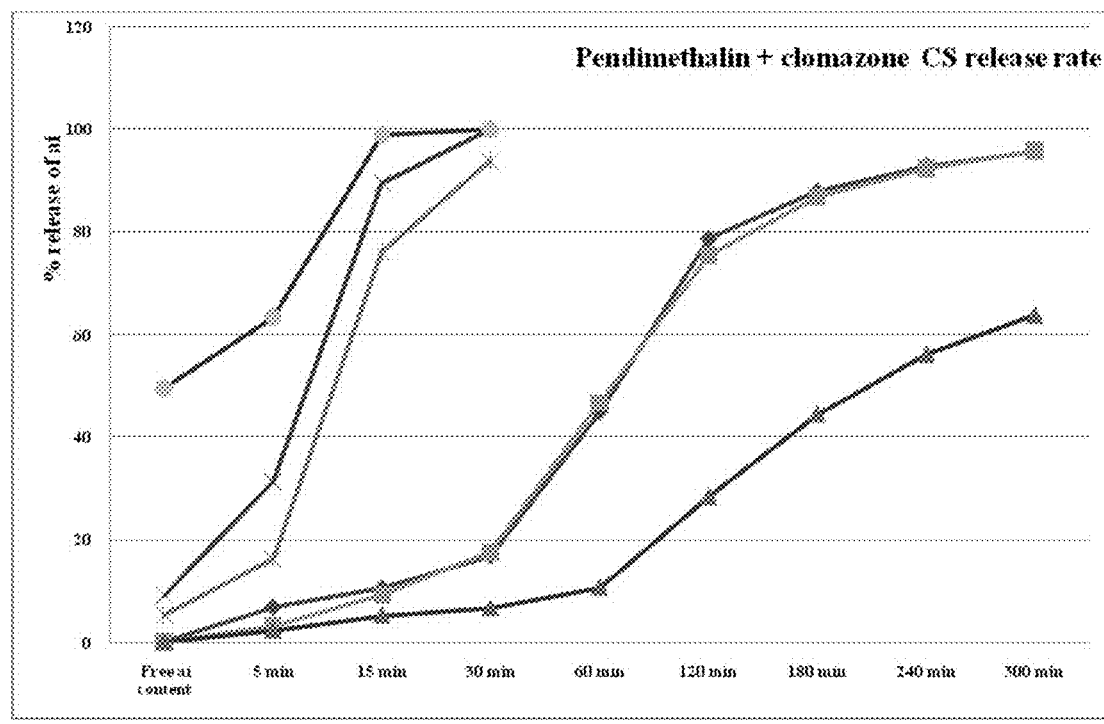
FIG. 1 compares the release rates of the capsules formulations according to the present invention. The pendimethalin release rate is measured from 3.5% capsules (fourth graph from top), 5.5% capsules (fifth graph from top), and 3.5% physical mixture of capsules (sixth graph from top). The clomazone release rate is measured from 3.5% capsules (second graph from top), 5.5% capsules (third graph from top) and 5.5% mixture of capsules (first graph from top). It was found that the increasing wall thickness from 3.5% to 5.5% delayed the release of clomazone while it did not significantly alter the release rate of pendimethalin. It was thus concluded that the present invention achieved a control of the release rate of both pendimethalin and clomazone, particularly by controlling the percentage wall strength and owing to the simultaneous presence of clomazone and pendimethalin.

It has been surprisingly found that the presence of an alkali or alkaline earth metal salt of an organic acid within the microencapsulated formulation of pendimethalin provides a substantially non-staining formulation. The term "substantially non-staining" herein denotes that such formulations comprising an alkali or alkaline earth metal salt of an organic acid demonstrates surprisingly reduced staining property by a fraction of at least two to about five times in comparison with the conventional formulations comprising an inorganic salt.

It has further been found that the microencapsulated formulations according to the present invention comprising an alkali or alkaline earth metal salt of an organic acid also reduce or eliminate the phytotoxicity that was observed with conventional formulations comprising an inorganic salt. Moreover, the addition of an alkali or alkaline earth metal salt of an organic acid does not increase the hardness of water which was observed with the conventional formulations thereby enhancing the suspension stability of the resultant formulations. It was surprising that use of an organic salt of an alkali or alkaline earth metal led to a drastic improvement in the suspension stability of the formulations according to the present invention. The present inventors have further found that the presence of an inorganic salt was shown to corrode the container while an organic salt did not corrode the container in which it was placed and/or prepared. The formulations according to the present invention were found to be storage stable. Without wishing to be bound by theory, it is believed that the presence of an alkali or alkaline earth metal salt of an organic acid further prevents the early rupture of the polymeric capsule wall.

In an embodiment, the microencapsulated formulations of the present invention comprise at least another herbicide, which may be either co-microencapsulated with pendimethalin or may be unencapsulated or may be microencapsulated separately and admixed with microencapsulated pendimethalin in a predetermined ratio. In an embodiment, the preferred co-herbicide is clomazone.

Clomazone has been known to be used with a high boiling inert organic solvent in order to reduce its volatility, such as in U.S. Pat. No. 5,583,090 or U.S. Pat. No. 5,597,780. It has been surprisingly found that encapsulated pendimethalin, when formulated together with clomazone, eliminates the need for clomazone to be dissolved in an organic solvent and yet does not lead to an increase in the volatility and therefore unintended plant injury due to clomazone volatility. Thus, a substantial reduction in the volatility of clomazone was observed when it was formulated with encapsulated pendimethalin without requiring the presence of an organic solvent.

In one embodiment, clomazone may be co-microencapsulated with pendimethalin, wherein both of these herbicides are co-encapsulated together within the microcapsules.

In another embodiment, unencapsulated clomazone is co-formulated with encapsulated pendimethalin to provide the capsule suspension formulations according to the present invention.

In another embodiment, encapsulated clomazone is admixed with encapsulated pendimethalin in a predetermined ratio.

Thus, in one aspect, the present invention provides a capsule suspension formulation comprising;
  microencapsulated pendimethalin comprising a herbicidally effective amount of pendimethalin being encapsulated within a polymeric wall, said polymeric wall being in-situ formed by an interfacial polymerization reaction occurring between a first phase dispersed in a second phase, at least one of said first and second phases being characterized in comprising a pre-defined amount of at least one alkali or alkaline earth metal salt of an organic acid; and
  a second herbicide.

Preferably, the second herbicide may be co-microencapsulated with pendimethalin or it may be unencapsulated or it may be encapsulated separately and admixed with encapsulated pendimethalin in a predetermined ratio.

Therefore, in this aspect, the present invention provides a capsule suspension formulation of microencapsulated pendimethalin and a second herbicide;
  said microencapsulated pendimethalin comprising a herbicidally effective amount of pendimethalin being encapsulated within a polymeric wall, said polymeric wall being in-situ formed by an interfacial polymerization reaction occurring between a first phase dispersed in a second phase, at least one of said first and second phases being characterized in comprising a pre-defined amount of at least one alkali or alkaline earth metal salt of an organic acid; and
  said second herbicide being either co-microencapsulated with pendimethalin or being unencapsulated or being microencapsulated separately and mixed with microencapsulated pendimethalin in a predetermined ratio.

In an embodiment, the selection of the second herbicide is not particularly limiting. The second herbicide may be any herbicide that is known in the art. Preferably, the second herbicide is a volatile herbicide i.e. a herbicide that is known to be volatile. It is usually desirable in the art to reduce or suppress the volatility of these notoriously volatile herbicides. The present invention surprisingly results into suppression of the volatility of the second herbicide.

In an embodiment, the second herbicide is a herbicide that is susceptible to vapor drift. Typically such herbicides are short chain ester herbicides such as 2,4-D esters, MCPA esters, triclopyr and picloram.

Preferably, the second herbicide is clomazone.

In another embodiment, the second herbicide is clomazone. It has been surprisingly found that the presence of encapsulated pendimethalin, either within the same microcapsule or being present as separate microcapsules, reduces the volatility of clomazone thereby surprisingly reducing the off-site injury while simultaneously reducing the staining problem in pendimethalin. Further, the surprising reduction in volatility of clomazone in the presence of microencapsulated pendimethalin was observed irrespective of whether or not clomazone was encapsulated, and when it was encapsulated, irrespective of whether it was co-microencapsulated within the same microcapsule or was microencapsulated separately. Especially, it was found that co-microencapsulating clomazone with pendimethalin within the same microcapsule led to substantially reduced clomazone free content and controlled release rate of clomazone with reduced vapor pressure thereby causing reduced off-site injury caused due to clomazone.

Thus, in this aspect, the present invention provides a capsule suspension formulation of microencapsulated pendimethalin and a second herbicide being clomazone;
  said microencapsulated pendimethalin comprising a herbicidally effective amount of pendimethalin being encapsulated within a polymeric wall, said polymeric wall being in-situ formed by an interfacial polymerization reaction occurring between a first phase dispersed in a second phase, at least one of said first and second phases being characterized in comprising a pre-defined amount of at least one alkali or alkaline earth metal salt of an organic acid; and
  said second herbicide clomazone being either co-microencapsulated with pendimethalin or being unencapsulated or being microencapsulated separately and mixed with microencapsulated pendimethalin in a predetermined ratio.

It was considered surprising as the use of an organic solvent, particularly a high boiling inert organic solvent is known to reduce the volatility of clomazone. It has been found that co-microencapsulating clomazone with pendimethalin within the same microcapsule or admixing microencapsulated pendimethalin with unencapsulated clomazone or microencapsulated clomazone eliminates the need for clomazone to be dissolved in a high boiling inert organic solvent prior to being encapsulated.

In a preferred embodiment, said first and second phases are preferably an aqueous phase and an organic phase. It should be understood however that said aqueous and organic phases are not particularly limiting. The interfacial polymerization reactions suitable for encapsulated formulations according to the present invention may be prepared by reaction between the wall forming components present in two substantially immiscible liquids, of which said organic and aqueous phases constitute a preferred embodiment. Moreover, the two walls forming components may be either same or different.

In another aspect, the present invention provides a process for the preparation of a capsule suspension formulation, said process comprising:
(a) forming an aqueous solution comprising at least one surfactant and a pre-defined amount of at least one alkali or alkaline earth metal salt of an organic acid;
(b) forming an organic phase by melting a herbicidally effective amount of pendimethalin active ingredient and a second herbicide and adding a predetermined amount of polyisocyanate wall forming component;
(c) dispersing said organic phase in said aqueous solution to obtain an emulsion to form an interface between the discrete droplets of organic phase and the aqueous phase; and
(d) maintaining said emulsion for a sufficient period of time to allow substantial completion of the self-polymerization reaction of polyisocyanate such that said liquid droplets in the organic phase are converted to capsules comprising polyurea shells enclosing pendimethalin active ingredient.

In an embodiment, the second herbicide is preferably clomazone. However, it is not essential to co-microencapsulate clomazone as beneficial reduction in the volatility of clomazone is observed when (a) unencapsulated clomazone is admixed with microencapsulated pendimethalin; and when (b) separately encapsulated clomazone is admixed with separately encapsulated pendimethalin and the microcapsules are mixed in a predetermined ratio.

Thus, in another aspect, the present invention also provides a process for the preparation of a capsule suspension formulation, said process comprising:
(a) forming an aqueous solution comprising at least one surfactant and a pre-defined amount of at least one alkali or alkaline earth metal salt of an organic acid;
(b) forming an organic phase by melting a herbicidally effective amount of pendimethalin active ingredient, at least a second herbicide and adding a predetermined amount of a first wall component to said organic phase;
(c) dispersing said organic phase in said aqueous solution to obtain an emulsion; and
(d) adding a second wall forming component to said emulsion such that said second wall forming component reacts with said first wall forming component comprised within said emulsion to polymeric wall encapsulating at least said herbicidally effective amount of pendimethalin active ingredient.

The capsule polymeric wall of the present invention may be any known shell wall material and is preferably selected from a polyurea, a polyurethane, a polyamide, a polycarbonate, a polysulfonamide shell wall or a crosslinked or non-crosslinked combinations thereof. Preferably, the capsule polymeric wall is a polyurea wall.

The capsule polymeric wall of the present invention is formed using interfacial polymerization by contacting said first wall forming component with a second wall forming component as is conventionally known in the art.

The first wall forming component is preferably selected from a polyisocyanate, a polyacid chloride, a polychloroformate and a polysulfonyl chloride. The second wall forming component is preferably selected from a polyamine and polyol. Preferably, a polyisocyanate reacts with a polyamine to form a polyurea capsule wall of the present invention.

The preferred polyisocyanates as the first wall forming component may be selected from tetramethylene diisocyanate, pentamethylene diisocyanate, hexamethylene diisocyanate, toluene diisocyanate, diphenylmethene-4,4'-diisocyanate, polymethylene polyphenylene isocyanate, 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4'4"-triphenylmethane triisocyanate. A preferred polyisocyanate first wall forming component is polymethylene polyphenylisocyanate.

The preferred polyamines as the second wall forming components may be selected from ethylenediamine, propylene-1,3-diamine, tetramethylenediamine, pentamethylenediamine, 1,6-hexamethylenediamine, diethylenetriamine, triethylenetetramine, tetraethylenepentamine, pentaethylenehexamine, 4,9-dioxadodecane-1,12-diamine, 1,3-phenylenediamine, 2,4- and 2,6-toluenediamine and 4,4'-diaminodiphenylmethane or acid addition salt thereof. The preferred polyamine according to the present invention is diethylenetriamine.

The first wall forming component comprises from about 0.1% to about 20% by weight of the organic phase of the present invention. The second wall forming component is preferably present in an amount of about 0.3% to 7.5% by weight relative to the total weight of the formulation.

In a further preferred embodiment, the preferred polyurea polymeric shell wall may be formed by a self-condensation reaction of a polyisocyanate wall forming component. In this embodiment, the process for the preparation of the capsule suspension formulation according to the present invention comprises establishing a physical dispersion of an organic phase in the aqueous phase. In this embodiment, the organic phase comprises the organic isocyanate intermediate such as hereinabove described along with the pendimethalin active ingredient.

Thus, in another aspect, the present invention provides a process for the preparation of a capsule suspension formulation, said process comprising:
(a) forming an aqueous solution comprising at least one surfactant and a pre-defined amount of at least one alkali or alkaline earth metal salt of an organic acid;
(b) forming an organic phase by melting a herbicidally effective amount of pendimethalin active ingredient and a herbicidally effective amount of clomazone and adding a predetermined amount of polyisocyanate wall forming component;
(c) dispersing said organic phase in said aqueous solution to obtain an emulsion to form an interface between the discrete droplets of organic phase and the aqueous phase; and
(d) maintaining said emulsion for a sufficient period of time to allow substantial completion of the self-polymerization reaction of polyisocyanate such that said liquid droplets in the organic phase are converted to capsules comprising polyurea shells enclosing pendimethalin active ingredient.

In an embodiment, the emulsion of said organic phase in said aqueous solution may be preferably heated to a temperature of between 20° C. to about 100° C., preferably to about 35-85° C. to accelerate the self-condensation of the polyisocyanate pre-polymer.

However, irrespective of whether self condensation of the first wall forming component is preferred or condensation between a first and a second wall forming component is preferred, the relative quantities of the organic and the aqueous phases are not critical for the process of the present invention. Typically, the organic phase may comprise upto about 75% by volume of the total emulsion and comprises discrete droplets of an organic solution dispersed in the aqueous solution.

The droplet size in the emulsion was not found critical to the formulation and process of the present invention but may be found between 0.5 microns to about 4000 microns, which may be further adapted using a high shear device to preferably about 1 micron to about 100 microns. It has further been found that the in situ self condensation polymerization reaction is self terminating and is generally allowed to run to completion. The reaction typically runs to completion within the span of a few minutes to a few hours. In a preferred embodiment, the reaction is typically allowed to run for about 2 to 3 hours.

However, the preferred polyurea polymeric shell may be formed by a self-condensation reaction of a preferred polyisocyanate using other preferred methods. In one such preferred embodiment, the formation of the polyurea capsule enclosure around the dispersed organic droplets could be brought about by (a) dispersing the organic phase droplets in the continuous aqueous phase to form an emulsion followed by heating the emulsion resulting therefrom; or (b) heating the continuous aqueous phase and dispersing the organic phase droplets in the heated continuous aqueous phase to form the emulsion thereby effecting the desired self-condensation reaction at the interface between the organic droplets and the aqueous phase.

The alkali or alkaline earth metal salt of an organic acid as used herein is preferably selected from alkali or alkaline earth metal salt of a weak organic acid selected from acetic acid, propionic acid, citric acid, fumaric acid, tartaric acid, oxalic acid, succinic acid, valeric acid, malonic acid, glutaric acid, adipic acid and phthalic acid.

The preferred alkali metal is selected from sodium and potassium. In a more preferred embodiment, the preferred alkali metal is sodium.

In another preferred embodiment, the alkali or alkaline earth metal salt of an organic acid is selected from sodium acetate or disodium succinate.

The aqueous solution comprises at least one surfactant. Preferably, the surfactant may be selected from the group comprising ethoxylated lignosulfonic acid salts, lignosulfonic acid salts, oxidized lignins, lignin salts, salts of styrene-maleic anhydride copolymers, polyvinyl alcohol, salts of partial esters of styrene-maleic anhydride copolymers, partial salts of polyacrylic acid and partial salts of polyacrylic acid terpolymers.

Preferably, the surfactant is lignosulfonate of calcium or sodium.

Preferably, the surfactant is present in an amount of about 0.2% to about 5% by weight of the formulation.

The aqueous solution of the present invention includes an alkali or alkaline earth metal salt of an organic acid or mixtures thereof in an amount of from about 2% to about 55% by weight of the formulation.

The term "herbicidally effective amount" of pendimethalin or clomazone is that quantity of pendimethalin or clomazone respectively which when applied in that amount will provide the required control of weeds. The particular amount is dependent upon many factors including, for example, the crop, weeds sought to be controlled and environmental conditions. The selection of the proper quantity of active agent to be applied, however, is within the expertise of one skilled in the art and is not considered particularly limiting.

The microencapsulated formulations according to the present invention comprise from about 5% to about 60% of pendimethalin active ingredient.

In a preferred embodiment, the polymeric shell wall according to the present invention constitutes from about 1% by weight to about 20% by weight of the formulation. In another preferred embodiment, the polymeric shell wall constitutes about 2.5% by total weight of the formulation.

The microcapsules of the present invention preferably have a particle size of about 2 micrometers to 50 micrometers.

Preferably, the capsule suspension formulations of the present invention comprise an anti-foam in an amount of about 0.01% to about 5% by weight of the formulation. Such suitable anti-foams are conventionally known in the art and are not particularly limiting.

The capsule suspension of the present invention may further include a rheology modifier. The preferred rheology modifier includes xanthan gum and clay, which may be present in an amount of about 0.01% to about 3% by weight of the formulation.

The capsule suspension formulation according to the present invention may further be neutralized with a mineral acid to regulate the pH within the desired range. Accordingly, the formulations according to the present invention additional comprises from about 0.1% to about 10% of a neutralizing acid, which may be a mineral or an organic acid. Preferably, the mineral acid is hydrochloric acid.

Another advantage of the addition of a neutralizing acid is that the added acid combines with the unreacted amines to form an ammonium salt, which substantially reduces the amount of external salt addition required for achieving an appreciable non-staining property. The addition of a neutralizing acid is particularly beneficial in reducing the level of inorganic salt of the prior art formulations, which has been reported to aggravate the problem of phytotoxicity in various tested plants. In this embodiment of the present invention, a significantly large quantity of amines in excess may be employed to further reduce the external addition of a salt by in situ generation of a larger amount of salt upon reaction with the neutralizing acid.

In a preferred embodiment, the formulations according to the present invention may additionally comprise a biocide in an amount of from about 0.01% to about 3% by weight of the formulation.

In another aspect, the present invention also provides a process for the preparation of a capsule suspension formulation, said process comprising:
   (a) forming an aqueous solution comprising at least one surfactant and a pre-defined amount of at least one alkali or alkaline earth metal salt of an organic acid and optionally heating said aqueous solution;
   (b) forming an organic phase by melting a herbicidally effective amount of pendimethalin active ingredient and a herbicidally effective amount of clomazone and adding a predetermined amount of a first wall component to said organic phase;
   (c) dispersing said organic phase in said aqueous solution to obtain an emulsion and optionally heating said formed emulsion; and
   (d) adding a second wall forming component to said emulsion such that said second wall forming component reacts with said first wall forming component comprised within said emulsion to polymeric wall encapsulating at least said herbicidally effective amount of pendimethalin active ingredient.

Preferably, said step of forming an aqueous solution comprises heating tap water to an elevated temperature, preferably about 60° C. and adding said surfactant and said alkali or alkaline earth salt of an organic acid. In a preferred embodiment, an anti-foam is also added to said aqueous solution.

In another preferred embodiment, said first wall forming component is preferably added to said molten pendimethalin while stirring. In an embodiment, a herbicidally effective of clomazone, when added to molten pendimethalin, eliminates the need for clomazone to be dissolved in a high boiling inert organic solvent thereby eliminating the use of an organic solvent.

In yet another preferred embodiment, said step of dispersing said organic phase in said aqueous solution to obtain an emulsion is carried out to a desired particle size.

In another preferred embodiment, subsequent to the addition of the second wall forming component to the emulsion, the reaction is allowed to continue for a predetermined time, preferably one hour under stirring while the reaction is maintained at an elevated temperature.

Subsequently, the reaction mixture is neutralized with an inorganic acid, preferably hydrochloric acid. The neutralization is carried out preferably to attain a formulation pH of from about 6.5 to about 7.5.

Subsequently, xanthan gum is preferably added under stirring.

In a preferred embodiment, a biocide is added to obtain the target formulation.

In a preferred embodiment, the process of the present invention is carried out at an elevated temperature to maintain the pendimethalin active ingredient in a molten state and to enhance the rate of polymeric wall formation. In this embodiment, the process of the present invention is preferably carried out at a temperature of about 35° C. to about 85° C., and is more preferably conducted at a temperature of about 50° C. to 65° C.

The release rate of the formulations according to the present invention preferably varied from about 100 ng to about 145 ng, while the free active ingredient was measured from about 0% to about 0.2% by weight of the formulation.

In another embodiment of the present invention, clomazone is encapsulated separately and admixed with microencapsulated pendimethalin in a predetermined ratio. In this embodiment, microencapsulated clomazone is separately produced by a microencapsulation process. In this embodiment, a herbicidally effective amount of clomazone is encapsulated within a polymeric shell wall of microcapsules. In this embodiment, clomazone is preferably dissolved in a stabilizing effective amount of at least one adjuvant selected from epoxidized derivatives of fatty acids or esters thereof and polymers and copolymers of terpenes, the organic solution obtained thereby is thereafter encapsulated. In an embodiment, the preferred adjuvant is selected from an epoxidized oleochemical and low molecular weight polymers and copolymers of terpenes. Preferably, an epoxidized oleochemical is selected from epoxidized soybean oil and epoxidized linseed oil although other epoxidized vegetable oils are not excluded.

Preferably, the low molecular weight terpenes includes pinene polymers and homopolymers and copolymers thereof. Still more preferably, the preferred pinene polymers are α- and β-pinene copolymers and/or Piccolyte AO. Preferably, the aforesaid α- and β-pinene copolymers are manufactured by various processes that include formation of a dimer, trimer or a polymer of α- and β-pinene.

Thus, in another aspect, the present invention provides a storage stable capsule suspension formulation comprising:
  microencapsulated pendimethalin, said microencapsulated pendimethalin comprising a herbicidally effective amount of pendimethalin being encapsulated within a polymeric wall, said polymeric wall being in-situ formed by an interfacial polymerization reaction occurring between a first phase dispersed in a second phase, at least one of said first and second phases being characterized in comprising a pre-defined amount of at least one alkali or alkaline earth metal salt of an organic acid; and
  microencapsulated clomazone, said microencapsulated clomazone comprising a herbicidally effective amount of clomazone encapsulated within a polymeric shell wall of microcapsules, said microcapsules characterized in comprising a stabilizing effective amount of at least one adjuvant selected from epoxidized derivatives of fatty acids or esters thereof and polymers and copolymers of terpenes;
  wherein the storage stable capsule suspension formulation comprises said microencapsulated pendimethalin and microencapsulated clomazone admixed in a predetermined ratio.

In this embodiment, the polymeric wall encapsulating clomazone is formed by an interfacial polymerization reaction occurring between an organic phase dispersed in an aqueous phase. In a preferred embodiment, the organic phase comprises a stabilizing effective amount of at least one adjuvant selected from epoxidized derivatives of fatty acids or esters thereof and polymers and copolymers of terpenes.

In this embodiment, the presence of the aqueous and organic phases for interfacial polymerization encapsulating clomazone are not particularly limiting. The interfacial polymerization reactions suitable for encapsulated clomazone component of the capsule suspension formulations according to the present invention may be prepared by reaction between the wall forming components present in two substantially immiscible liquids, of which said organic and aqueous phases constitute a preferred embodiment. Moreover, the two walls forming components may be either same or different or these same or different wall forming components may be comprised within the first phase only or in the second phase only or distributed between said first and second immiscible phases.

In another aspect, the present invention provides a process for the preparation of a capsule suspension formulation, said process comprising:
  (a) preparing encapsulated pendimethalin component by a process comprising forming an aqueous solution comprising at least one surfactant and a pre-defined amount of at least one alkali or alkaline earth metal salt of an organic acid; forming an organic phase by melting a herbicidally effective amount of pendimethalin active ingredient and adding a predetermined amount of polyisocyanate wall forming component; dispersing said organic phase in said aqueous solution to obtain an emulsion to form an interface between the discrete droplets of organic phase and the aqueous phase; and either maintaining said emulsion for a sufficient period of time to allow substantial completion of the self-polymerization reaction of polyisocyanate such that said liquid droplets in the organic phase are converted to capsules comprising polyurea shells enclosing pendimethalin active ingredient or adding a second wall forming component to said emulsion such that said second wall forming component reacts with said first wall forming component comprised within said emulsion to polymeric wall encapsulating at least said herbicidally effective amount of pendimethalin active ingredient;

(b) preparing encapsulated clomazone component by a process comprising forming an aqueous solution comprising at least one surfactant; forming an organic phase by adding a herbicidally effective amount of clomazone to a stabilizing effective amount of at least one adjuvant selected from epoxidized derivatives of fatty acids or esters thereof and polymers and copolymers of terpenes and adding a first wall forming component to said organic phase; dispersing said organic phase in said aqueous solution to obtain an emulsion; and adding a second wall forming component to said emulsion and allowing said second wall forming component to react with said first wall forming component comprised within said emulsion to form a polymeric wall encapsulating said herbicidally effective amount of clomazone; and (c) admixing said encapsulated pendimethalin and encapsulated clomazone components in a predetermined ratio.

In an embodiment, the capsule polymeric wall encapsulating the clomazone component of the present invention may be any known shell wall material and is preferably selected from a polyurea, a polyurethane, a polyamide, a polycarbonate, a polysulfonamide, a urea formaldehyde, a melamine formaldehyde resin, a melamine urea resin, a gelatine/gum arabic shell wall or crosslinked or non-crosslinked combinations thereof. Preferably, the capsule polymeric wall is a polyurea wall.

In this embodiment, the polymeric shell wall of the clomazone component may be prepared using substantially the method that is described above for the preparation of the pendimethalin component.

In an embodiment of the process for the preparation of the clomazone component, dispersing said aqueous solution in said organic phase to obtain the emulsion comprises mixing said aqueous solution in the organic phase at high speed agitation in order to obtain an emulsion. Preferably, the emulsion comprises particles between 0.1 microns to 200 microns, preferably between 1 micron and 50 microns and more preferably between 2 microns and 10 microns.

In another embodiment of the process for the preparation of the clomazone component, allowing said wall forming components to react with each other comprises allowing a chemical reaction to occur with or without heat for a predetermined amount of time until complete polymerization occurs. Preferably, complete polymerization of the wall forming components occurs between 15 minutes and 5 hours, preferably between half an hour and 4 hours and more preferably between half an hour and 2 hours.

The interfacial polymerization between the wall forming components can be carried at ambient temperature or at an elevated temperature. Accordingly, the temperature range for the reaction is between 5° C. and 90° C., preferably between 10° C. and 70° C. and more preferably between 15° C. and 60° C.

In another embodiment of the process for the preparation of the clomazone component, allowing said wall forming components to react with each other comprises maintaining the emulsion for a sufficient period of time to allow substantial completion of the polymerization reaction between said wall forming components such that the liquid droplets in the organic phase are converted to capsules comprising polyurea shells enclosing clomazone active ingredient.

The capsule polymeric wall of the clomazone component of the present invention is formed using interfacial polymerization by contacting said second wall forming component added to the aqueous solution with a first wall forming component present within the organic phase as is conventionally known in the art. The first wall forming component is preferably selected from a polyisocyanate, a polyacid chloride, a polychloroformate and a polysulfonyl chloride. The second wall forming component is preferably selected from a polyamine and/or polyol. Preferably, a polyisocyanate reacts with a polyamine to form a polyurea capsule wall of the present invention.

The preferred polyisocyanates as the first wall forming component may be selected from tetramethylene diisocyanate, pentamethylene diisocyanate, hexamethylene diisocyanate, toluene diisocyanate, diphenylmethene-4,4'-diisocyanate, polymethylene polyphenylene isocyanate, 2,4,4'-diphenyl ether triisocyanate, 3,3'-dimethyl-4,4'-diphenyl diisocyanate, 3,3'-dimethoxy-4,4'-diphenyl diisocyanate, 1,5-naphthylene diisocyanate and 4,4'4"-triphenylmethane triisocyanate. A preferred polyisocyanate first wall forming component is toluene diisocyanate or polymethylene polyphenylisocyanate.

The preferred polyamines as the second wall forming components may be selected from ethylenediamine, propylene-1,3-diamine, tetramethylenediamine, pentamethylenediamine, 1,6-hexamethylenediamine, diethylenetriamine, triethylenetetramine, tetraethylenepentamine, pentaethylenehexamine, 4,9-dioxadodecane-1,12-diamine, 1,3-phenylenediamine, 2,4- and 2,6-toluenediamine and 4,4'-diaminodiphenylmethane or acid addition salt thereof. The preferred polyamine according to the present invention is selected from ethylenediamine, diethylenetriamine, triethylenetetramine and tetraethylenepentamine.

The first wall forming component present within the organic phase comprises from about 2% to 25% by weight of the organic phase, preferably from 5% to 20% by weight. The second wall forming component present in the aqueous phase represents from 0.3% to 7% by weight of the total weight of the formulation, preferably 1% to 5% by weight.

The relative quantities of the organic and the aqueous phases are not critical for the process of the present invention. Typically, the organic phase may comprise up to about 75% by volume of the total emulsion and comprises discrete droplets of an organic phase dispersed in the aqueous solution.

The droplet size in the emulsion was not found critical to the formulation and process of the present invention but may be found between 0.1 microns to 200 microns, preferably between 1 micron and 50 microns, which may be further adapted using a high shear device to preferably about 2 microns to about 10 microns.

In an embodiment, the wall forming reaction during the preparation of the clomazone component typically runs to completion within the span of a few minutes to a few hours. In a preferred embodiment, the reaction is typically allowed to run for about half an hour till about 2 to 3 hours.

The aqueous solution comprises at least one surfactant. Preferably, the surfactant may be selected from the group comprising ethoxylated lignosulfonic acid salts, lignosulfonic acid salts, oxidized lignins, lignin salts, salts of styrene-maleic anhydride copolymers, polyvinyl alcohol, salts of partial esters of styrene-maleic anhydride copolymers, partial salts of polyacrylic acid and partial salts of polyacrylic acid terpolymers.

Preferably, the surfactant is lignosulfonate of calcium or sodium or mixtures thereof or a modified kraft lignin with a high sulfonic acid group or a combination thereof in any suitable proportion.

Preferably, the surfactant is present in an amount of about 0.5% to about 1.5% by weight of the formulation.

The term "herbicidally effective amount" of clomazone is that quantity of clomazone which when applied in that amount will provide the required control of weeds. The particular amount is dependent upon many factors including, for example, the crop, weeds sought to be controlled and environmental conditions. The selection of the proper quantity of active agent to be applied, however, is within the expertise of one skilled in the art and is not considered particularly limiting.

A stabilizing effective amount of a adjuvant for the clomazone component is selected from epoxidized derivatives of fatty acids or esters thereof and polymers and copolymers of terpenes is an amount sufficient to substantially increase the plasticity of the encapsulating polymeric shell wall and consequently minimize the volatility of clomazone to produce a storage stable agrochemical composition having a commercially reasonable shelf life of at least about 2 years. For example, a stabilizing effective amount of adjuvant selected from epoxidized derivatives of fatty acids or esters thereof and polymers and copolymers of terpenes can be upto about 70% by weight of the organic phase in the formulation.

The microencapsulated formulations according to the present invention comprise from about 10% to about 50% of clomazone active ingredient by weight of the clomazone component of the capsule suspension formulation of the invention.

In a preferred embodiment, the polymeric shell wall according to the present invention constitutes from about 20% by weight to about 40% by weight of the organic phase in the clomazone component in the formulation. In another preferred embodiment, the polymeric shell wall constitutes about 31% by total weight of the organic phase in the clomazone component of the formulation.

Preferably, the clomazone component of the formulations of the present invention comprises an anti-foam in an amount of about 0.01% to about 5% by weight of the clomazone component. Such suitable anti-foams are conventionally known in the art and are not particularly limiting.

The capsule suspension of the present invention may further include a rheology modifier. The preferred rheology modifier includes xanthan gum and/or clay, which may be present in an amount of about 0.01% to about 1% by weight of the clomazone component of the formulation.

The capsule suspension formulation according to the present invention may further be neutralized with a mineral acid to regulate the pH within the desired range. Accordingly, the formulations according to the present invention additionally comprises from about 0.1% to about 10% of a neutralizing acid, which may be a mineral or an organic acid. Preferably, the mineral acid is hydrochloric acid.

In a preferred embodiment, the formulations according to the present invention may additionally comprise a biocide in an amount of from about 0.01% to about 3% by weight of the formulation.

In a most preferred embodiment, said epoxidized fatty ester is an epoxidized oleochemical and more preferably is epoxidized soybean oil. In a further preferred embodiment, the preferred stabilizing agent may be a polymer or a copolymer of terpenes.

The preferred epoxidized fatty esters according to the present invention may further be selected from epoxidized palm oil, epoxidized rapeseed oil, epoxidized sunflower oil, epoxidized peanut oil, epoxidized cottonseed oil, epoxidized palm kernel oil, epoxidized coconut oil, epoxidized soybean oil, epoxidized olive oil and epoxidized linseed oil. Preferably, epoxidized soybean oil or epoxidized linseed oil may be used. However, it should be understood that the choice of the particular vegetable oil is not particularly limiting.

The preferred polymers and copolymers of terpenes includes low molecular weight saturated or unsaturated polymers and copolymers of terpenes. These polymers and copolymers of terpenes may be preferably selected from $\alpha$- and $\beta$-pinene copolymers, chemically modified terpenes such as terpenoids, rosins, rosin esters, terpene polyamides, styrenated terpenes, terpene phenolics, phenol-modified copolymer of styrene and alpha methyl styrene with terpenes.

In an embodiment, the capsule suspension formulation of the present invention comprises a mixture of the pendimethalin component and the clomazone component in a predetermined ratio. In an embodiment, the pendimethalin component and the clomazone component are admixed in ratio of from about 1:10 to about 10:1.

In another non-limiting embodiment, the pendimethalin component and the clomazone component are admixed in a ratio of from about 1:2 to about 1:3.

The invention further relates to a method for controlling weeds at a locus by applying to the locus of the weeds a herbicidally effective amount of a microencapsulated pendimethalin, said microencapsulated pendimethalin either being co-encapsulated with clomazone or being admixed in a predetermined ratio with unencapsulated clomazone or encapsulated clomazone.

Preferably, the present invention provides a method for controlling undesirable plant species which comprises applying to the foliage of the plants or to the soil or water containing seeds or other propagating organs thereof, a herbicidally effective amount of a microencapsulated pendimethalin, said microencapsulated pendimethalin either being co-encapsulated with clomazone or being admixed in a predetermined ratio with unencapsulated clomazone or encapsulated clomazone.

In an embodiment of the aforesaid aspect of the invention, the method comprises administering encapsulated pendimethalin in the locus of the weeds or to the foliage of the plants or to the soil or to water containing seeds or other propagating organs, wherein said locus or soil or foliage of water is also administered unencapsulated or encapsulated clomazone either concurrently or sequentially in any sequence. Preferably, clomazone is co-microencapsulated with pendimethalin and applied concurrently to the desired site.

In an embodiment, either the encapsulated pendimethalin component or the encapsulated clomazone could be administered first, followed by the sequential administration of the remaining component. Thus, in this embodiment, the method comprises administering a first encapsulated component in the locus of the weeds or to the foliage of the plants or to the soil or to water containing seeds or other propagating organs, wherein said locus or soil or foliage of water is also administered the second encapsulated component either concurrently or sequentially in any sequence. In this embodiment, the first encapsulated component is encapsulated pendimethalin and the second encapsulated component is encapsulated clomazone.

In another embodiment, the first encapsulated component is encapsulated clomazone and the second encapsulated component is encapsulated pendimethalin.

Therefore, in another aspect, the present invention also provides a combination kit for administration to a locus of the weeds or to the foliage of the plants or to the soil or to water containing seeds or other propagating organs, said combination kit comprising:
(a) a first encapsulated component;
(b) a second encapsulated component;
(c) an instruction manual comprising instructions for administering the two encapsulated components.

In an embodiment of this aspect of the invention, the first encapsulated component is encapsulated pendimethalin and the second encapsulated component is encapsulated clomazone.

In another embodiment of this aspect of the invention, the first encapsulated component is encapsulated clomazone and the second encapsulated component is encapsulated pendimethalin.

Preferably, clomazone is co-microencapsulated with pendimethalin and applied concurrently to the desired site.

In an embodiment, the combination kit of the present invention includes an instruction manual. The instruction manual includes instructions for administering the two encapsulated components.

In an embodiment, the instruction manual includes instructions for administering the encapsulated components at a locus or to a foliage of the plants or to the soil or to water containing seeds or other plant propagating organs.

In another embodiment, the instruction manual includes instructions for admixing the first encapsulated component with a second encapsulated component in a predetermined ratio. In an embodiment, the instruction manual instructs an user to admix the pendimethalin component and the clomazone component in a ratio of from about 1:10 to about 10:1, preferably in a ratio of from about 1:2 to 1:3.

In yet another embodiment, the instruction manual includes instructions for administering the encapsulated components sequentially. In this embodiment, the instructions include administering the first encapsulated component followed by a sequential administration of the second encapsulated component after a predetermined amount of time. In this embodiment, the first encapsulated component is encapsulated pendimethalin and the second encapsulated component is encapsulated clomazone.

In another embodiment, the first encapsulated component is encapsulated clomazone and the second encapsulated component is encapsulated pendimethalin.

In an embodiment, the combination kit is packed in a package or a carton. In another embodiment, the instruction manual may be printed on said package or carton or may be printed on a booklet that may be included within the package or the carton.

Advantageously, the microcapsule formulations prepared according to the present invention or obtainable by the process of the present invention may be used directly as herbicidal compositions or may be diluted with water for use.

Alternatively, additional ingredients such as anti-settling agents, pH-adjusters, anti-freeze agents and the like may be added to the microcapsule compositions prepared by the process of the present invention to form concentrated microcapsule herbicidal compositions without departing from the scope of the present invention.

The invention shall now be described with reference to the following specific examples. It should be noted that the example(s) appended below illustrate rather than limit the invention, and that those skilled in the art will be able to design many alternative embodiments without departing from the scope of the present invention.

Example 1

An aqueous solution was created by heating tap water to 60° C. while adding sodium lignosulfonate and subsequently sodium acetate, then antifoam while stirring. A sufficient quantity of water was separately preserved for the amine and gum preparations. Meanwhile, organic phase was formed by melting pendimethalin technical to 60° C. and then adding polymethylene polyphenylisocyanante and a herbicidally effective amount of clomazone while stirring. The aqueous and organic phases were maintained at 60° C. throughout reaction. The organic phase was emulsified in the aqueous solution till the desired particle size. DETA (amine) was added to the resultant emulsion. Reaction was allowed to proceed for 1 hour while maintaining heat at 60° C. under stirring. The reaction mixture was allowed to cool to ambient temperature for 15 minutes before neutralizing with HCl. The formulation was neutralized to pH 8.0 in cold conditions or at a pH of 7 in warmer conditions. The neutralized formulation was filtered through a 60 mesh sieve. A xanthan gum—water slurry was separately prepared and added to the above formulation under strong stirring conditions for at least 15 minutes to have a complete development of the gum. Lastly, a biocide was added and the final product was filtered through a 60-mesh sieve. The particle size was measured using a Horiba LA-910 or CILAS 1064. The resultant formulation was compared to the properties of conventionally marketed formulation.

Table 1 below is the composition of the formulation obtained by the process described in the above process.

| Phase | Component | Example 1 |
| --- | --- | --- |
| Water phase | Water | 32.631 |
| | Sodium lignosulfonate | 2.5 |
| | Sodium acetate | 15.00 |
| Oil phase | Pendimethalin technical 27 @ 96% | 28.125 |
| | Polymethylene polyphenylisocyanante | 1.853 |
| | Clomazone 11.5 @ 96% | 11.917 |
| Amines | DETA (×2) | 0.954 |
| | Water | 3.00 |
| Others | Neutralizing acid | 1.020 |
| | Xathane 2% gum | 3.00 |

Staining Measurement

The staining measurements reported above were measured with the help of a Hunter LabScan XE colorimeter. Each reported test was repeated five times to confirm the staining or non-staining nature of the tested samples on different samples and under different testing conditions. In order to conclude the improvement in the non-staining properties of the formulations of the present invention, staining tests were conducted on duct tape and repeated to cloth tape to reconfirm the findings.

In the tests reported above, the colorimeter measured the staining color left on the substrate by assigning three values $L^*$, $a^*$ and $b^*$ to the stain which corresponded to the lightness/darkness measurement, redness/greenness measurement and the yellowness/blueness measurement respectively. The differences between these measured for each tested sample i.e. that according to the present invention and the conventionally known sample and that of a standard sample were calculated as delta (Δ) values respectively:

Δa*=a* (sample)−a* (standard), wherein +Δa* meant sample was redder than standard and −Δa* meant the sample was greener than the standard;

Δb*=b* (sample)−b* (standard), wherein +Δb* meant the tested sample was yellower than standard and −Δb* meant the sample was bluer than standard;

ΔL*=L* (sample)−L*(standard), wherein +ΔL* meant the sample was lighter than the standard and −ΔL* meant the sample was darker than the standard.

The total color or staining value, ΔE, was thereafter calculated using the following formula:

$$\Delta E = \text{SQRT} \left[ (\Delta L^*)^2 + (\Delta a^*)^2 + (\Delta b^*)^2 \right]$$

A greater value of ΔE corresponded to a greater degree of staining. The stain samples were prepared on cloth tape (Scotch Glass Cloth Electrical Tape) or duct tape—(Tesa, BDF Beiersdorf White Duct Tape). These tapes were chosen in order to investigate possible differences in staining potential of the formulations on different surfaces. The substrates consisted of 2 inch by 2 inch (5 cm by 5 cm) squares cut from transparent paper with a piece of tape on the center. Enough formulation was applied to the tapes to create a ¾ inch (2 cm) diameter circle. The formulations were left on the tape for 15 minutes and then rinsed off completely with a water squirt bottle. Color/stain testing was then performed within 30 minutes of when samples were rinsed. Blank samples of tapes without formulation were tested first on the equipment to subtract out color values inherent to the tapes themselves. Stain samples were prepared in duplicate and each sample was measured twice, once in a horizontal orientation and once in a vertical orientation on the colorimeter to cancel the effects of the tape's directional grain. This yielded four data points for each stain sample. Therefore, the total staining measurement for the sample according to the invention and for the conventional samples was calculated for cloth tape and duct tape using the above formula. Without wishing to be bound by theory, it was believed that pendimethalin having an intense staining property, would tend to adsorb strongly on organic surfaces such as polyester, cloth, paper etc. Hence, it was believed that a comparison of the common surfaces such as first aid tape, cloth tape, duct tape would provide a close reflection of actual staining a farmer would encounter as a daily routine.

It was thus surprisingly found that the capsule suspension formulation of the present invention, and more specifically the encapsulated pendimethalin component thereof, afforded a substantially non-staining activity upon its use. The staining effect was found to have reduced by a fraction of about 5 or at least by a fraction of about 2 comparative to the hitherto known formulation containing encapsulated pendimethalin.

Specifically, it was surprisingly found that the pendimethalin component of the capsule suspension formulation according to the present invention displayed a staining DE of only 2.44 and 1.49 on cloth tape and duct tape respectively, whereas the closest commercial formulation displayed a staining measurement of 11.22 and 2.19 respectively. Without wishing to be bound by theory, it is believed that the presence of an alkali or alkaline earth metal salt of an organic acid prevented the rupture of the polymeric capsule wall and reduced the staining property of the conventional microencapsulated pendimethalin formulations, and consequently the staining properties of the capsule suspension formulation of the present invention.

Further staining tests were conducted on various substrates comparing the staining property of the encapsulated pendimethalin component of the capsule suspension formulations according to the present invention comprising other organic salts of alkali and alkaline earth metals vis-à-vis the formulations comprising an inorganic salt. Again, greater ΔE represented greater staining.

Table 2 demonstrates the cumulative stain value measurements total for cloth tape and first aid tape for the pendimethalin component of the capsule suspension formulation according to the present invention comprising disodium succinate versus a commercially available encapsulated pendimethalin formulation comprising an inorganic salt, which is further compared to a formulation substantially free of a salt. It was surprisingly found that the formulation comprising disodium succinate (8.600) was only half as staining as the commercially available formulation (16.348).

| ΔE | Cloth Tape | First aid tape | Sum |
|---|---|---|---|
| Commercial formulation | 7.453 | 8.895 | 16.348 |
| No salt | 7.735 | 18.220 | 25.955 |
| Disodium succinate | 4.220 | 4.380 | 8.600 |

($\Delta E_{SD} = 0.5$)

Table 3 demonstrates the stain value measurements total for cloth tape for the encapsulated pendimethalin component of the capsule suspension formulation according to the present invention comprising sodium acetate versus a commercially available encapsulated pendimethalin comprising an inorganic salt, which is further compared to a formulation substantially free of a salt. It was surprisingly found that the formulation comprising sodium acetate (2.780) was only a third as staining as the commercially available formulation (7.453).

| ΔE | Cloth tape |
|---|---|
| Sodium acetate | 2.780 |
| Commercial formulation | 7.453 |
| No salt | 7.735 |

($\Delta E_{SD} = 0.5$)

Table 4 demonstrates the stain value measurements for first aid tape for the encapsulated pendimethalin component of the capsule suspension formulation according to the present invention comprising disodium succinate versus a commercially available formulation comprising an inorganic salt, which is further compared to a formulation substantially free of a salt. It was surprisingly found that the formulation comprising disodium succinate (4.380) was only half as staining as the commercially available formulation (8.895).

| ΔE | First aid tape |
|---|---|
| Disodium succinate | 4.380 |
| Commercial formulation | 8.895 |
| No salt | 18.220 |

($\Delta E_{SD} = 0.5$)

Figure 2:
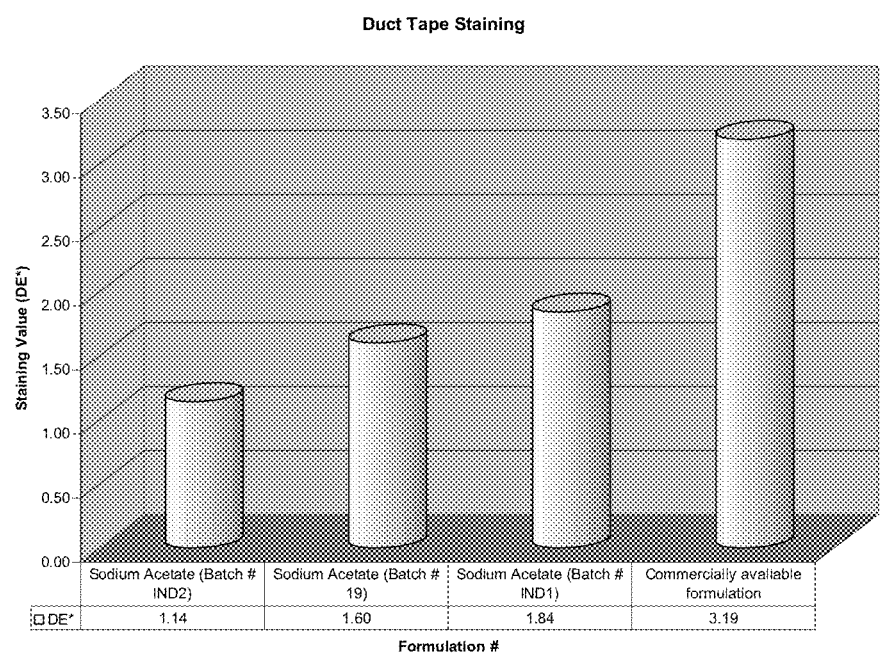
FIG. 2 compares the staining value measured in $\Delta E$ of sodium acetate in duct tape staining.

FIG. 2 depicts a comparison of three separate sodium acetate formulations having the same formulation as the pendimethalin component of the present invention vis-à-vis the staining measured for commercial formulation measured on a duct tape. All three batches comprising sodium acetate exhibited ΔE values of 1.14, 1.60 and 1.84 which was only about half of the ΔE exhibited by the commercial formulation, 3.19.

Figure 3:
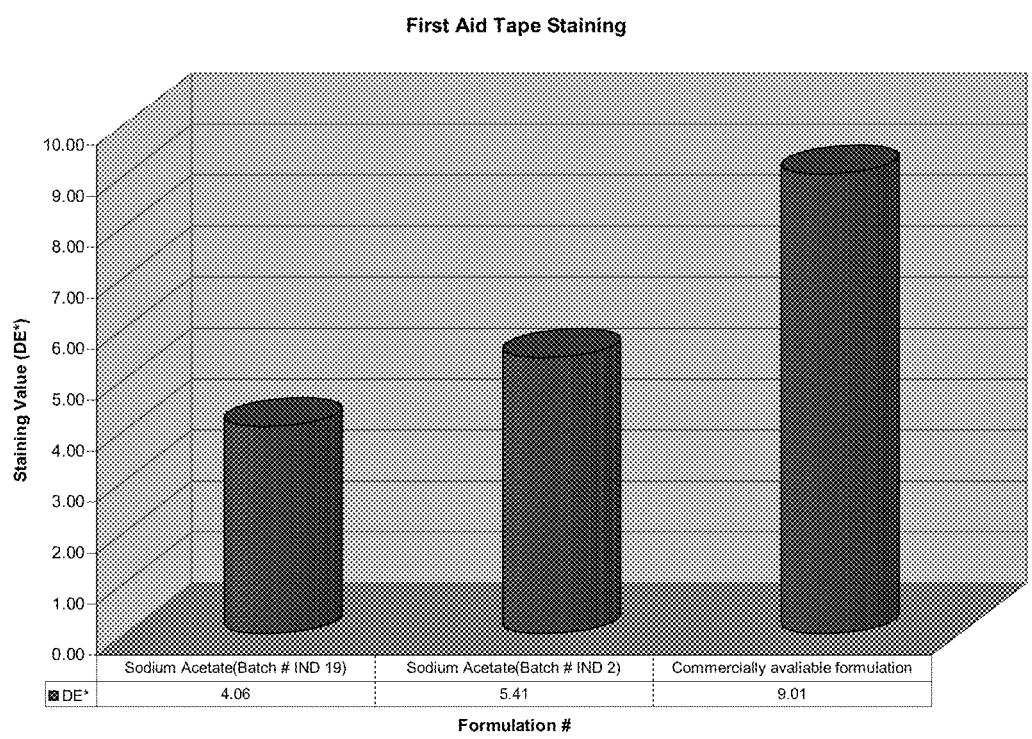
FIG. 3 compares the staining value measured in $\Delta E$ of sodium acetate in first aid tape staining.

FIG. 3 depicts a comparison of two separate sodium acetate formulations having the same formulation as the pendimethalin component of the present invention vis-à-vis the staining measured for commercial formulation measured on a first aid tape. The two batches comprising sodium acetate exhibited ΔE values of 4.06 and 5.41 which was only about half of the ΔE exhibited by the commercial formulation, 9.01.

Figure 4:
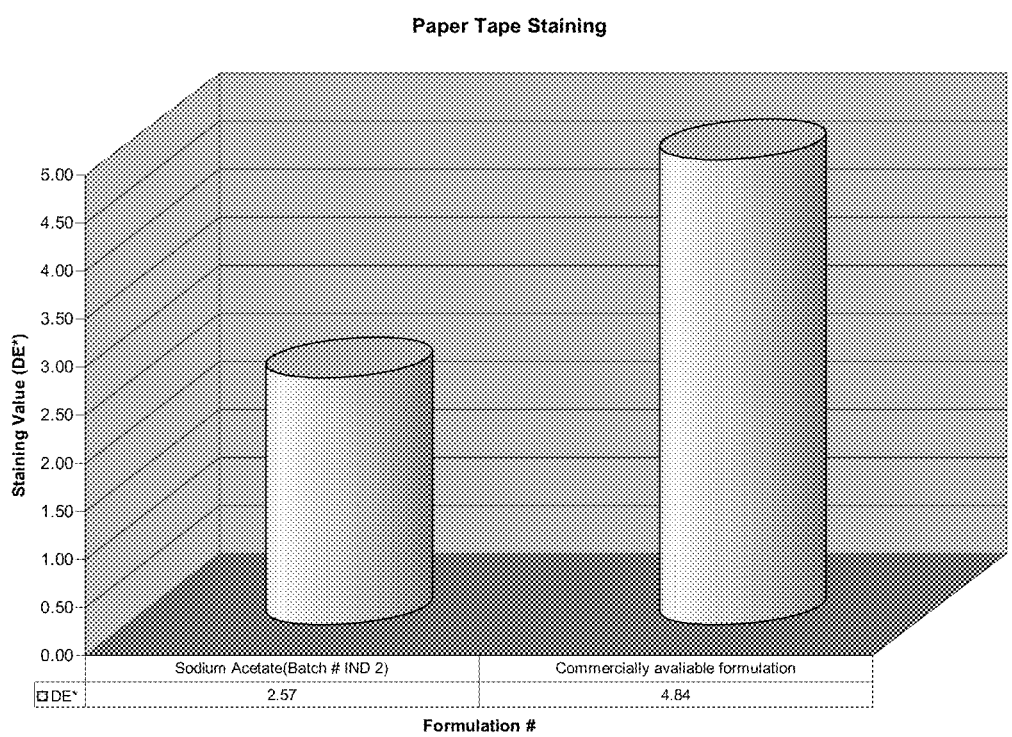
FIG. 4 compares the staining value measured in $\Delta E$ of sodium acetate in paper tape staining.

FIG. 4 depicts a comparison of sodium acetate formulation as the pendimethalin component of the present invention vis-à-vis the staining measured for commercial formulation measured on a paper tape. The batch comprising sodium acetate exhibited ΔE values of 2.57 which was only about half of the ΔE exhibited by the commercial formulation, 4.84.

Figure 5:
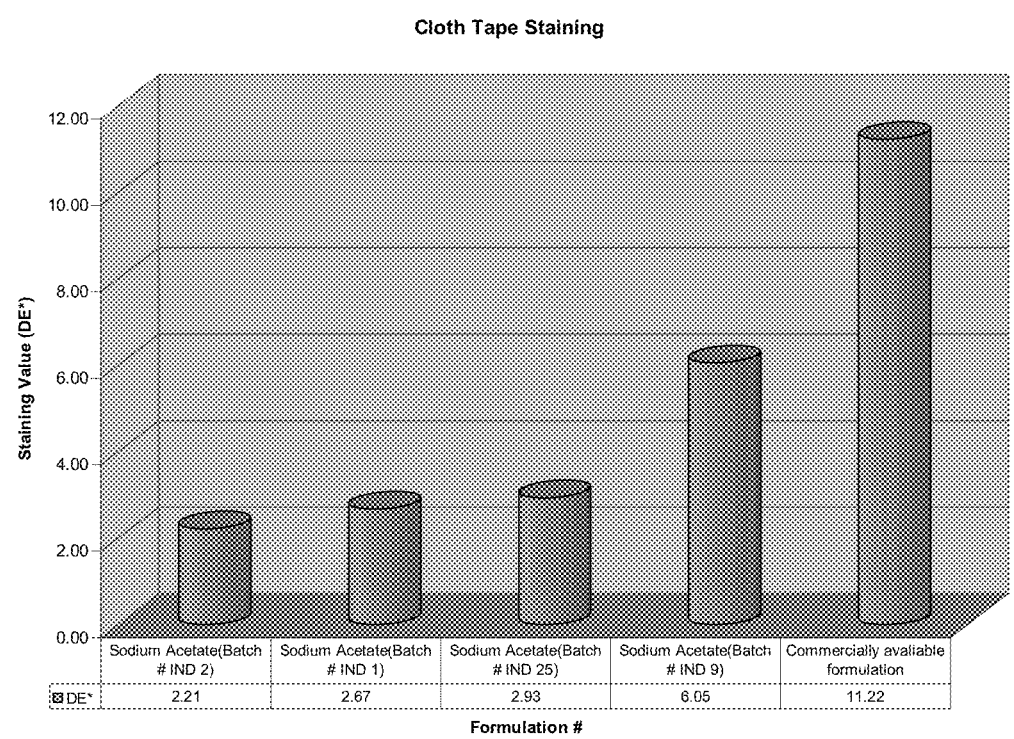
FIG. 5 compares the staining value measured in $\Delta E$ of sodium acetate in cloth tape staining.

FIG. 5 depicts a comparison of four separate sodium acetate formulations having the same formulation as the pendimethalin component of the present invention vis-à-vis the staining measured for commercial formulation measured on a cloth tape. The batches comprising sodium acetate exhibited ΔE values of 2.21, 2.67, 2.93 and 6.05 which was only about one-third to about half of the ΔE exhibited by the commercial formulation, 11.22.

Indirect Staining Evaluation:

The relative staining evaluation was performed indirectly by seeding the microcapsules formulation directly on scotch tape and observing after a time period of 2-3 hours. The pendimethalin stain was seen on the tapes after washing out the applied formulations. The extent of staining on the cloth tapes were determined quantitatively by extracting pendimethalin with methanol and analyzing it on GC.

Scotch Tape—231 was used for stain evaluation. A 4.8 cm×4.8 cm (23.04 $cm^2$ piece of tape was pasted in a petri-dish. The respective samples in an amount of 0.25-0.35 gram were applied on the tape and spread on the tape carefully. The formulations applied tapes were then kept for 2-3 hours at room temperature. The tapes were then washed under water shower without rubbing to remove the applied formulations. The tapes were then observed for pendimethalin stains. The stains were then quantified by extracting the deposited pendimethalin, which is primarily responsible for staining, with methanol. The deposited amount of pendimethalin was quantified by GC using internal standard method against standard pendimethalin solution. The results of the confirmatory pendimethalin staining experiments were tabulated as hereunder:

| Sample | Tape | Mg of Pendimethalin stain/$cm^2$ in 3 hr. | average Mg of Pendimethalin stain/$cm^2$ in 3 hr. | Rating of Pendimethalin staining in 3 hr. relative to the EC formulation |
|---|---|---|---|---|
| Pendimethalin 26.75% + clomazone 11.25% Co-encapsulated CS | scotch-1 scotch-2 | 0.00000488 0.00000312 | 0.00000400 | 0.26 |
| UPL-Pendimethalin 38.7% CS | scotch-1 scotch-2 | 0.00000480 0.00000448 | 0.00000464 | 0.30 |
| Commercially available sample comprising encapsulated pendimethalin comprising an inorganic salt 38.7% | scotch-1 scotch-2 | 0.00001200 0.00001264 | 0.00001232 | 0.79 |
| Pendimethalin 30% EC formulation | scotch-1 scotch-2 | 0.00166104 0.00144112 | 0.00155108 | 100.00 |

Conclusion:
1. The encapsulated pendimethalin component comprising an organic acid salt exhibited about 60% reduction in staining when applied alone in comparison to the commercially available encapsulated pendimethalin formulation.
2. The encapsulated pendimethalin component, when co-encapsulated with clomazone, exhibited a further 10-15% reduction in staining.

Example 2

The release rates of the capsule formulations according to the present invention were studied and the results are presented as table 1 appearing hereunder and the accompanying FIG. 1.

| Capsule type | Free active content | 5 min | 15 min | 30 min | 60 min | 120 min | 180 min | 240 min | 300 min |
|---|---|---|---|---|---|---|---|---|---|
| Pendimethalin release rate 3.5% capsule (third graph from top) | 0.13 | 7.01 | 10.72 | 16.79 | 44.9 | 78.7 | 87.82 | 92.8 | 95.9 |
| Pendimethalin release rate 5.5% capsule (fifth graph from top) | 0.09 | 3.19 | 9.3 | 17.54 | 46.65 | 75.33 | 86.72 | 92.3 | 95.78 |

-continued

| Capsule type | Free active content | 5 min | 15 min | 30 min | 60 min | 120 min | 180 min | 240 min | 300 min |
|---|---|---|---|---|---|---|---|---|---|
| Pendimethalin release rate 3.5% physical admixture of capsule (sixth graph from top) | 0.14 | 2.41 | 5.26 | 6.68 | 10.62 | 28.32 | 44.36 | 56.01 | 63.74 |
| Clomazone release rate 3.5% capsule (second graph from top) | 9.1 | 31.39 | 89.4 | 100 | — | — | — | — | — |
| Clomazone release rate 5.5% capsule (third graph from top) | 5.32 | 16.2 | 76.07 | 93.78 | — | — | — | — | — |
| Clomazone release rate 5.5% mixture of capsules (first graph) | 49.57 | 63.36 | 98.88 | 100 | — | — | — | — | — |

Example 3

Pendimethalin+Clomazone CS Admixture

A. Pendimethalin 42% CS Component (Concentrate)

| Batch size | % w/w |
|---|---|
| Pendimethalin tech 42 @96 | 43.750 |
| PMPI | 1.262 |
| Water | 35.638 |
| Sodium ligno sulphonate | 2.500 |
| Na-acetate | 15.000 |
| DETA | 0.650 |
| Defoamer, Biocide and Neutralizing acid | q.s. |
| Total | 100.000 |

Organic Phase Preparation:

A required quantity of pendimethalin, which was either pre-melted or powdered, was charged in a vessel. The technical was melted and the temperature of the active material was maintained at 62-67° C. throughout. A required quantity of PMPI was thereafter charged and stirred for homogeneity.

Organic Phase Preparation:

A required quantity of distilled water was charged into a vessel. Thereafter, sodium lignosulfonate was charged and stirred for dissolution. Anhydrous sodium acetate was then charged, stirred and maintained at 62-67° C.

Amine Solution:

About 3% water (out of the total calculated water quantity) was taken and charged the calculated quantity of amine. The solution was stirred for homogeneity.

Homogenization:

The aqueous phase was homogenized at a temperature of 62-67° C. at slow rpm of about 500 rpm. A defoamer was charged to the solution followed by the organic phase at 62-67° C. The resultant material as again homogenized at 6000 rpm to achieve a desired particle size $D_{100}$ in the range of 18-23 microns and $D_{50}$ in the range of 6-7.5 microns.

Microencapsulation:

The homogenized solution was taken at 62-67° C. and amine solution was added slowly while stirring. The stirring was continued while the temperature was maintained at 62-67° C. for one hour. The material was then cooled to room temperature at 25-35° C. The cooled material was neutralized to attain a pH of 7.4 to 7.8 using 35.5% hydrochloric acid solution.

B. Clomazone 35.3% CS Concentrate Component:

| Ingredients | % W/W |
|---|---|
| Clomazone tech | 36.510 |
| PMPI | 1.952 |
| Epoxidized soybean oil | 8.826 |
| sodium ligno sulphonate | 1.099 |
| Water | 37.72 |
| DETA | 0.987 |
| Neutralizing acid, Biocide, Defoamer and Calcium Chloride | 12.90 |

Organic Phase Preparation:

A required quantity of clomazone technical was charged in a vessel and epoxidized soybean oil was added. The resultant mixture was stirred to homogeneity. A required quantity of PMPI was again added and stirred for homogeneity.

Aqueous Phase Preparation:

A required quantity of distilled water was charged in a vessel and polyvinyl alcohol was added and stirred to obtain a solution. Sodium lignosulfonate was charged and stirred till dissolution.

Amine Solution Preparation:

About 3% of the calculated quantity of water was added to the required quantity of amine and stirred for homogeneity.

Homogenization:

The aqueous phase was homogenized at slow RPM (about 500 RPM) and defoamer was charged to the solution. The organic phase was then charged at room temperature and the mixture was homogenized at maximum RPM of about 6000

RPM. The particle size in the range of 18-23 microns and $D_{50}$ in the range of 6-7.5 microns was attained.

Encapsulation:

The homogenized solution above was taken to which the amine solution was added while stirring. The temperature was maintained at 50° C. for one hour and stirring was continued. The material was cooled after one hour to room temperature to 25-35° C. and calcium chloride was added. The mixture was stirred for homogeneity. The resulting material was neutralized to pH 7.4 to 7.8 using 34-37% hydrochloric acid solution.

C. Physical Mixture

| Parameter | Quantity | Active % required in formulation |
|---|---|---|
| Batch size | 100 g | |
| Encapsulated pendimethalin purity | 42 g | 26.76% w/w Pendimethalin |
| Encapsulated clomazone purity | 35.3 g | 11.24% w/w Clomazone |
| Preparation of the final mixed formulation | | |
| Encapsulated pendimethalin 27 g @ 42% purity | 64.29 | Encapsulated pendimethalin component |
| Clomazone 11.5 g @ 35.3% purity | 32.12 | Encapsulated clomazone component |
| Gum | 1.50 | Structuring agent |
| Biocide | 0.12 | Biocide |
| Water | 2.09 | Diluent |
| Total | 100.00 | |

Preparation of Xanthan Gum Gel:

98 gram water was taken and warmed to 65-70° C. Added 2 gram of xanthan gum with stirring and mixed further to obtain a homogenous gel.

The required quantity of the admixed encapsulated formulation was taken and stirred till homogeneity was achieved. Water was diluents was added and the mixture was stirred again. The resultant mixture was added to the xanthan gum solution prepared above to obtain the desired viscosity. The final product was analyzed and packed into suitable container.

Statement of One or More Advantages of the Invention

1. It was found that the formulation comprising a physical mix of separate microcapsules comprising clomazone and pendimethalin exhibited a fast release of clomazone and a slow release of pendimethalin.
2. It was found that in a formulation comprising clomazone and pendimethalin being co-microencapsulated, the presence of pendimethalin delayed the release of clomazone, which is desirable to achieve significantly lesser off-site injury caused to clomazone.
3. The increasing wall thickness from 3.5% to 5.5% further delayed the release of clomazone while it did not significantly alter the release rate of pendimethalin.
4. The present invention achieves a control of the release rate of both pendimethalin and clomazone, particularly by controlling the percentage wall strength and owing to the simultaneous presence of clomazone and pendimethalin.
5. The present invention achieves a reduced free active ingredient of pendimethalin and clomazone thereby causing substantially reduced staining and off-site injury of unintended plants.
6. The present invention reduces the phytotoxicity occurring due to clomazone by substantially reducing the vapor pressure of clomazone.
7. The presence invention substantially reduces the occurrence of staining due to pendimethalin.
8. The present invention achieves a long residual control of both pendimethalin and clomazone.
9. The present invention provides capsule suspension formulation that are substantially free of an organic solvent.

Wherein the aforegoing reference has been made to components having known equivalents, then such equivalents are herein incorporated as if individually set forth.

Accordingly, it will be appreciated that changes may be made to the above described aspects and embodiments of the invention without departing from the principles taught herein. Additional advantages of the present invention will become apparent for those skilled in the art after considering the principles in particular form as discussed and illustrated. Thus, it will be understood that the invention is not limited to the particular embodiments described or illustrated, but is intended to cover all alterations or modifications which are within the scope of the invention.

The invention claimed is:

1. A capsule suspension comprising;
    a formulation comprising: microencapsulated pendimethalin comprising a herbicidally effective amount of pendimethalin encapsulated within a polyurea polymeric wall;
    microcapsules encapsulating said pendimethalin, said microcapsules comprising polymeric wall of polyurea constituting from about 1% to about 20% by weight of the formulation;
    an aqueous phase comprising at least one alkali or alkaline earth metal salt of an organic acid selected from the group consisting of acetic acid, propionic acid, citric acid, fumaric acid, tartaric acid, succinic acid, valeric acid, malonic acid, glutaric acid, adipic acid and phthalic acid, wherein said at least one alkali or alkaline earth metal salt of an organic acid is present in an amount ranging from about 2% to about 55% by weight of the formulation; and
    a second herbicide, which may be co-microencapsulated with pendimethalin or it may be unencapsulated or it may be encapsulated separately and admixed with encapsulated pendimethalin;
    wherein said capsule suspension has reduced staining properties compared to a capsule suspension in which said alkali or alkaline earth metal salt of an organic acid is outside of said aqueous phase; and
    wherein said second herbicide displays delayed release and reduced free content in the presence of said encapsulated pendimethalin.

2. The capsule suspension as claimed in claim 1, wherein said second herbicide is co-encapsulated together with pendimethalin within the microcapsules.

3. The capsule suspension as claimed in claim 1, wherein said second herbicide is separately encapsulated and admixed with a herbicidally effective amount of encapsulated pendimethalin.

4. The capsule suspension formulation as claimed in claim 1, wherein said second herbicide is clomazone.

* * * * *